(12) United States Patent
Christiansen

(10) Patent No.: US 9,691,162 B2
(45) Date of Patent: Jun. 27, 2017

(54) ENDOSCOPIC IMAGE PROCESSING SYSTEM HAVING MEANS WHICH GENERATE GEOMETRIC MEASUREMENT INFORMATION IN THE DETECTION RANGE OF AN OPTICAL DIGITAL CAMERA

(76) Inventor: Olaf Christiansen, Potsdam (DE)

(*) Notice: Subject to any disclaimer, the term of this patent is extended or adjusted under 35 U.S.C. 154(b) by 981 days.

(21) Appl. No.: 14/004,229

(22) PCT Filed: Feb. 11, 2012

(86) PCT No.: PCT/DE2012/200007
§ 371 (c)(1),
(2), (4) Date: Feb. 3, 2015

(87) PCT Pub. No.: WO2012/107041
PCT Pub. Date: Aug. 16, 2012

(65) Prior Publication Data
US 2015/0161802 A1    Jun. 11, 2015

(30) Foreign Application Priority Data
Feb. 11, 2011    (DE) .................. 10 2011 011 671

(51) Int. Cl.
*G06T 7/60*    (2017.01)
*H04N 5/225*    (2006.01)
(Continued)

(52) U.S. Cl.
CPC .............. *G06T 7/60* (2013.01); *A61B 5/1076* (2013.01); *A61B 90/06* (2016.02); *A61B 90/361* (2016.02);
(Continued)

(58) Field of Classification Search
CPC ... G06T 7/60; G06T 7/70; G06T 2207/10068; G06T 2207/30; A61B 90/06;
(Continued)

(56) References Cited

U.S. PATENT DOCUMENTS 5,669,871 A  *  9/1997  Sakiyama ............ A61B 5/1076
                                                   348/135
6,295,368 B1 *  9/2001  Hasegawa ................ A61B 1/05
                                                   382/128
(Continued)

FOREIGN PATENT DOCUMENTS

IE    WO201061293 A2 *  6/2010  ............. A61B 1/313

*Primary Examiner* — Sath V Perungavoor
*Assistant Examiner* — Howard D. Brown, Jr.

(57) ABSTRACT

The invention relates to an endoscopic image processing system, which includes an optical digital camera, in particular having great depth of field, and means which, in the detection range of the optical digital camera, generate distance information which is processed together with the image information and is then detected and used in order to generate additional geometric data relating to the image content. The measurement information is obtained from an image of an auxiliary instrument which may be designed as a normal surgical instrument, wherein the image of a section of the auxiliary instrument is extracted from the camera image and serves as a reference parameter for the image scale. On this basis a piece of geometric information is then inserted, true to scale and in fixed relation to the auxiliary instrument, into the current camera image as a virtual measuring or display element. Said element can be an image scale, for example, which appears suspended on the auxiliary instrument in the image and can be "operated" therewith.

17 Claims, 8 Drawing Sheets

(51) Int. Cl.
*A61B 5/107* (2006.01)
*A61B 90/00* (2016.01)
*A61B 90/94* (2016.01)
*A61B 90/98* (2016.01)
*G06T 7/70* (2017.01)
*A61B 1/00* (2006.01)
*A61B 34/10* (2016.01)

(52) U.S. Cl.
CPC .............. *A61B 90/94* (2016.02); *A61B 90/98* (2016.02); *G06T 7/70* (2017.01); *H04N 5/2259* (2013.01); *A61B 1/00009* (2013.01); *A61B 1/00057* (2013.01); *A61B 2034/102* (2016.02); *A61B 2090/061* (2016.02); *F04C 2270/041* (2013.01); *G06T 2207/10068* (2013.01); *G06T 2207/30021* (2013.01); *H04N 2005/2255* (2013.01)

(58) Field of Classification Search
CPC ....... A61B 90/94; A61B 90/361; A61B 90/98; A61B 5/1076; A61B 2090/061; A61B 2034/102; H04N 5/2259; H04N 2005/2255; F04C 2270/041
See application file for complete search history.

(56) References Cited

U.S. PATENT DOCUMENTS

| | | | | |
|---|---|---|---|---|
| 6,806,899 | B1* | 10/2004 | Schaack | G02B 23/2407 348/65 |
| 2005/0228221 | A1* | 10/2005 | Hirakawa | A61B 1/00009 600/101 |
| 2008/0015412 | A1* | 1/2008 | Hori | A61B 1/00096 600/109 |
| 2009/0167847 | A1* | 7/2009 | Doi | A61B 1/00096 348/65 |
| 2011/0021874 | A1* | 1/2011 | Ogawa | A61B 5/6885 600/109 |
| 2011/0074950 | A1* | 3/2011 | Oka | A61B 1/042 348/137 |
| 2013/0018255 | A1* | 1/2013 | Kitamura | A61B 1/00009 600/424 |

* cited by examiner

[Fig. 1]
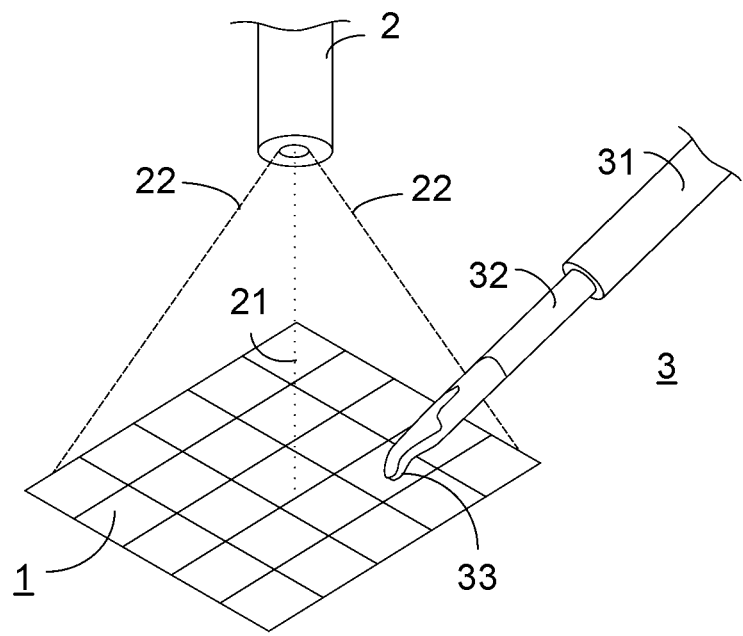
[Fig. 1a]
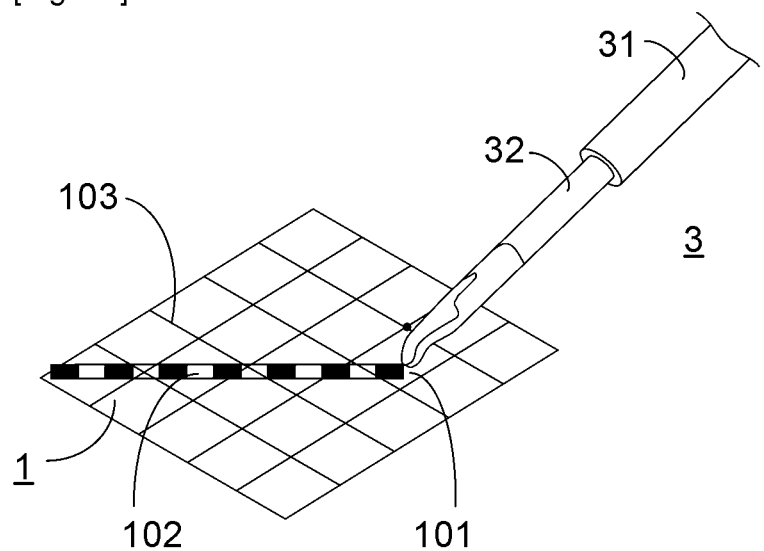

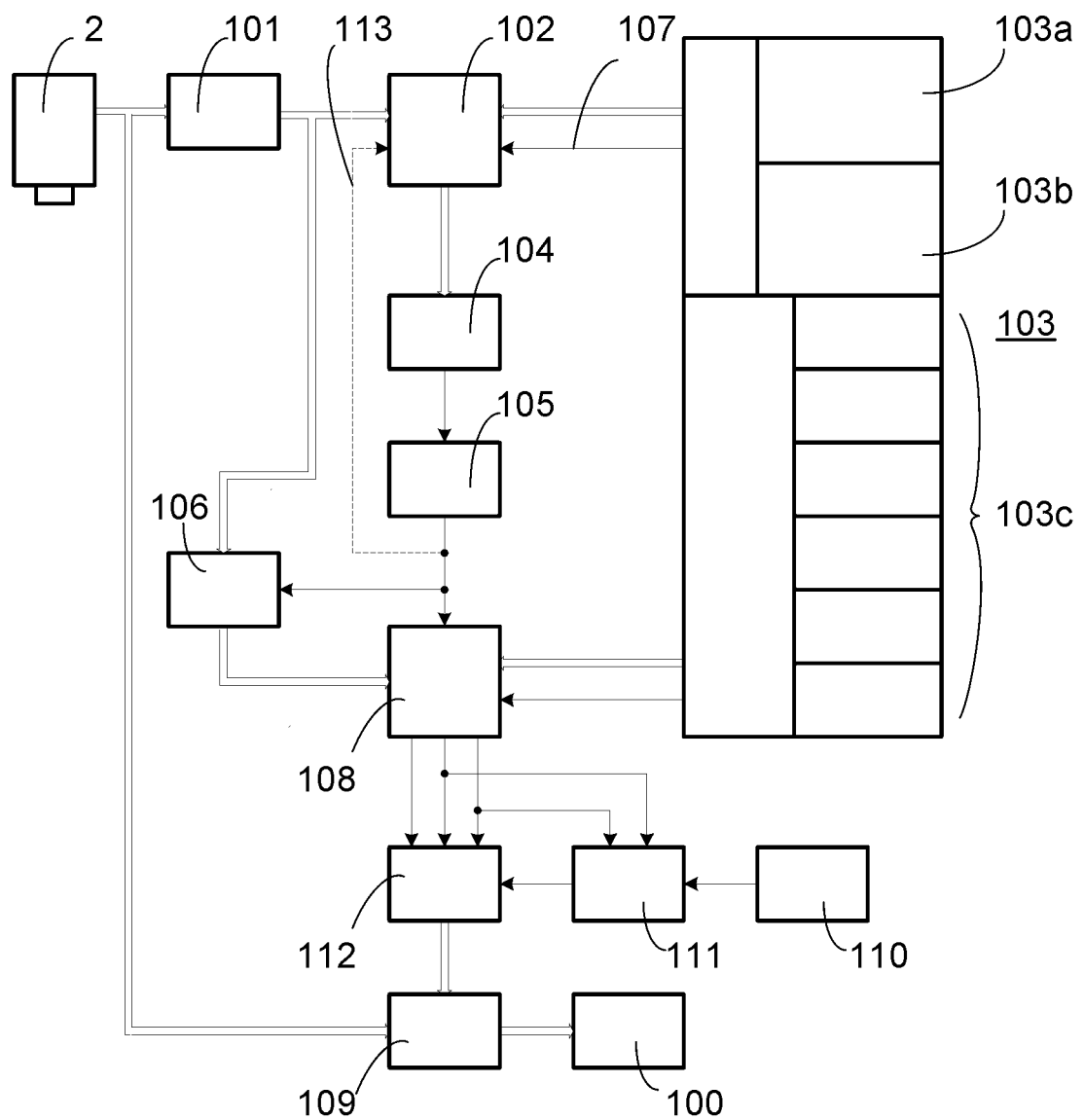
[Fig. 2]

[Fig. 3]
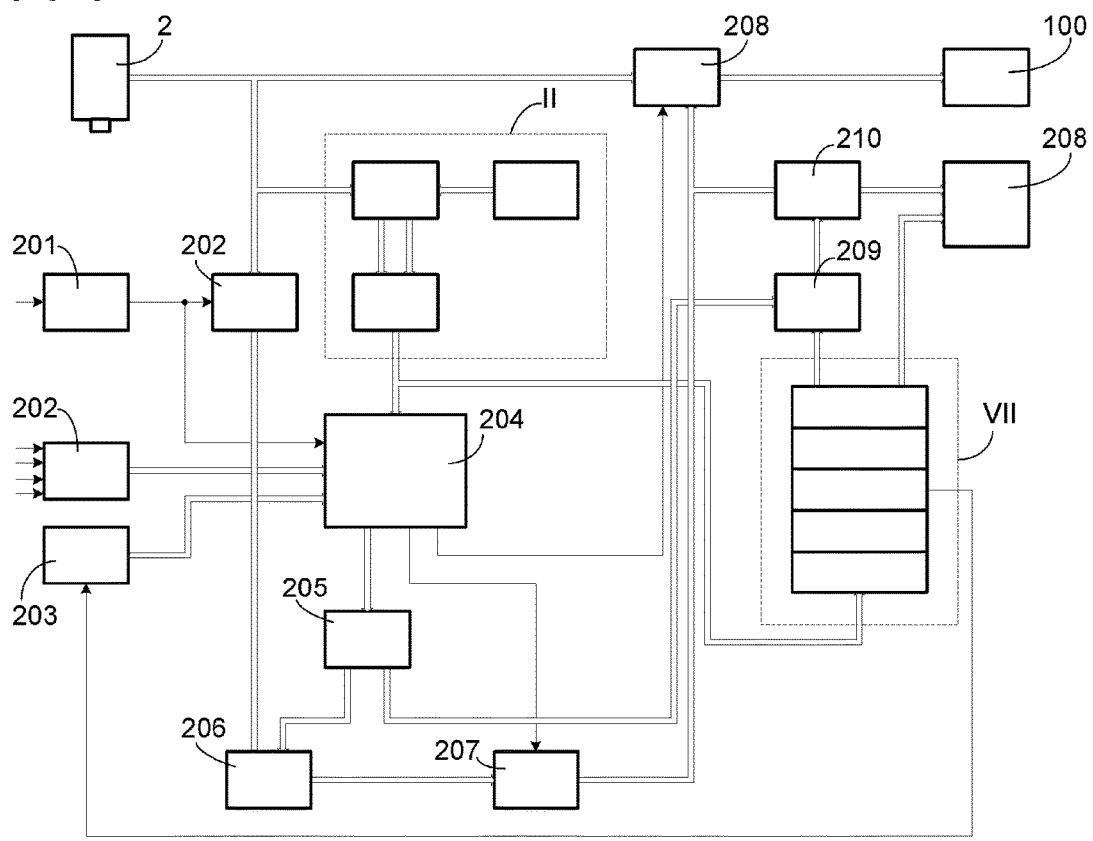
[Fig. 4]
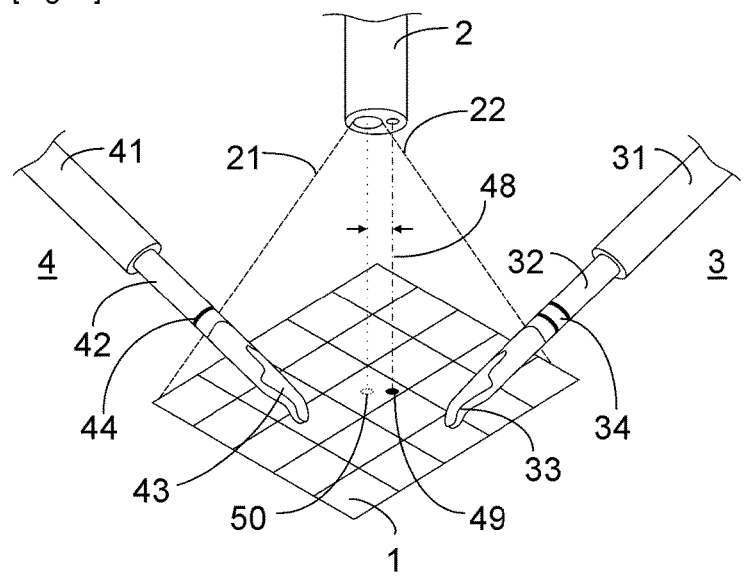

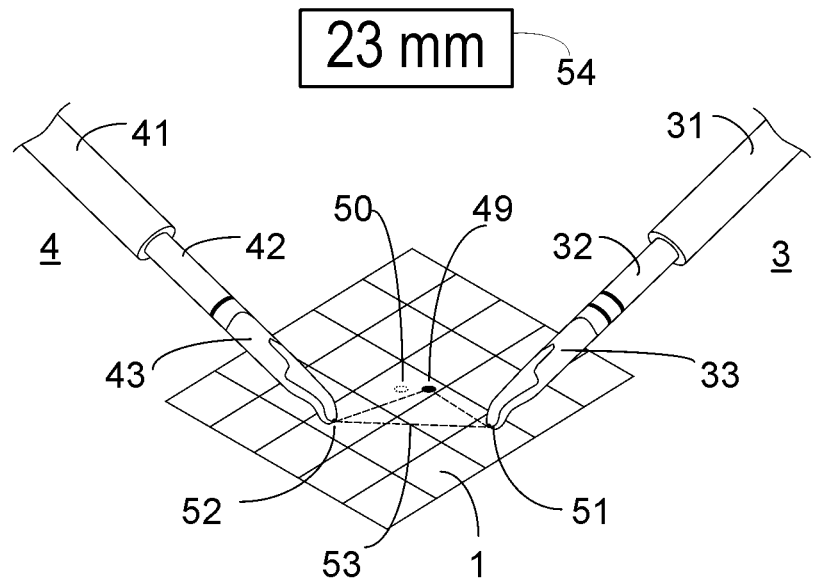
[Fig. 4a]
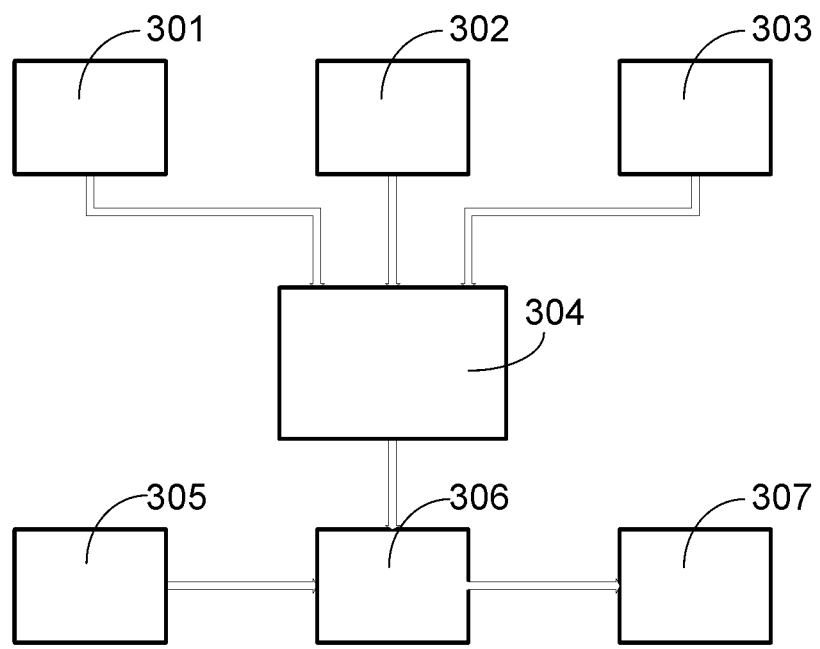
[Fig. 5]

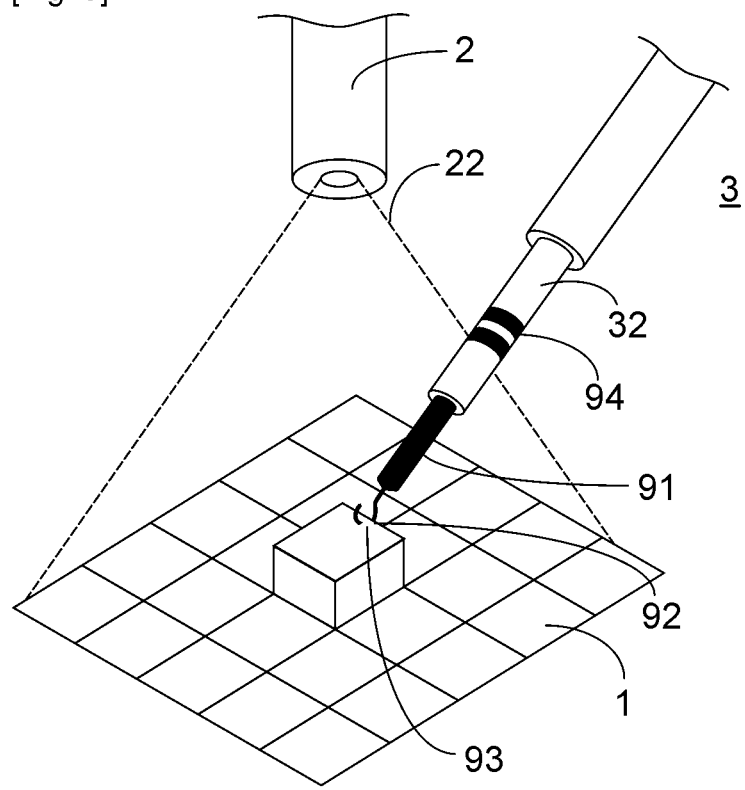
[Fig. 9]
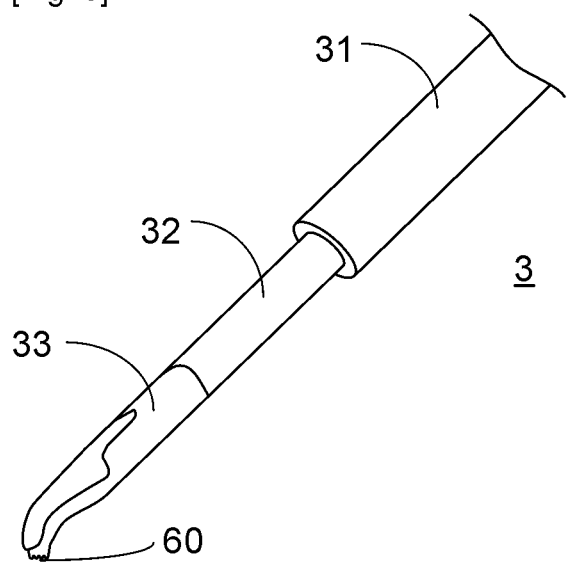
[Fig. 6]

[Fig. 6a]
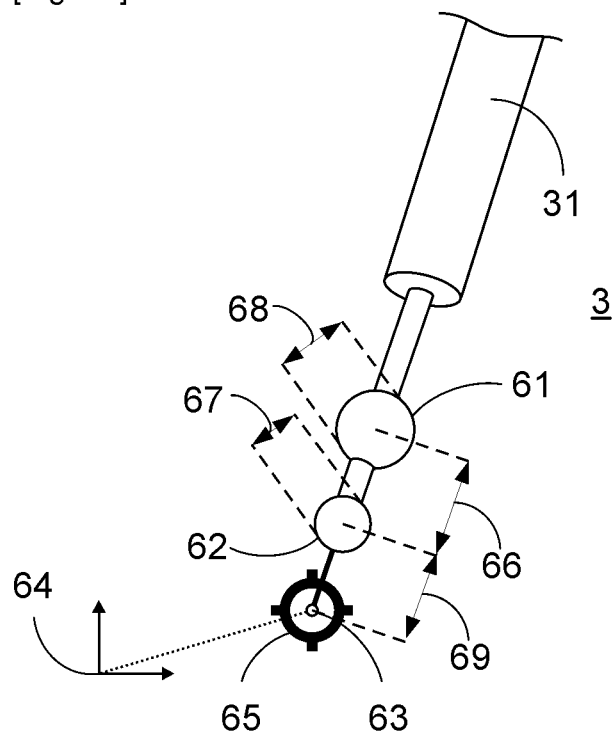
[Fig. 6b]
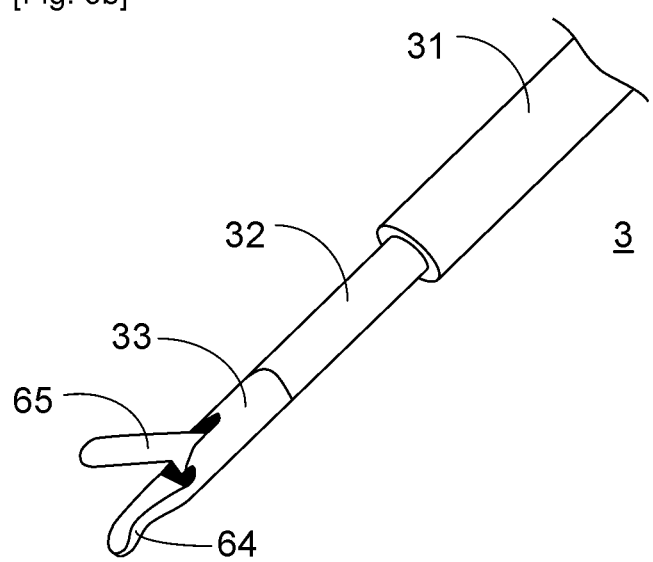

[Fig. 7]
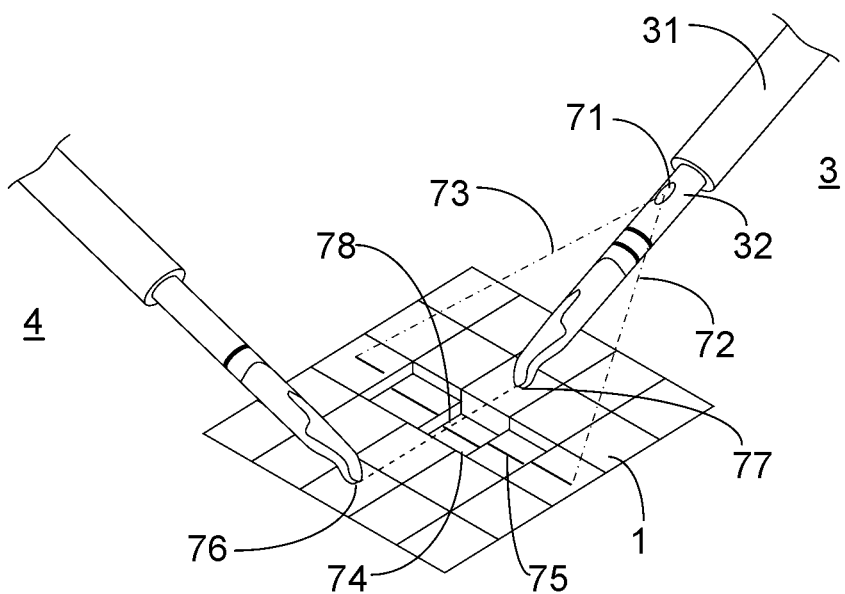
[Fig. 7a]
[Fig. 8]
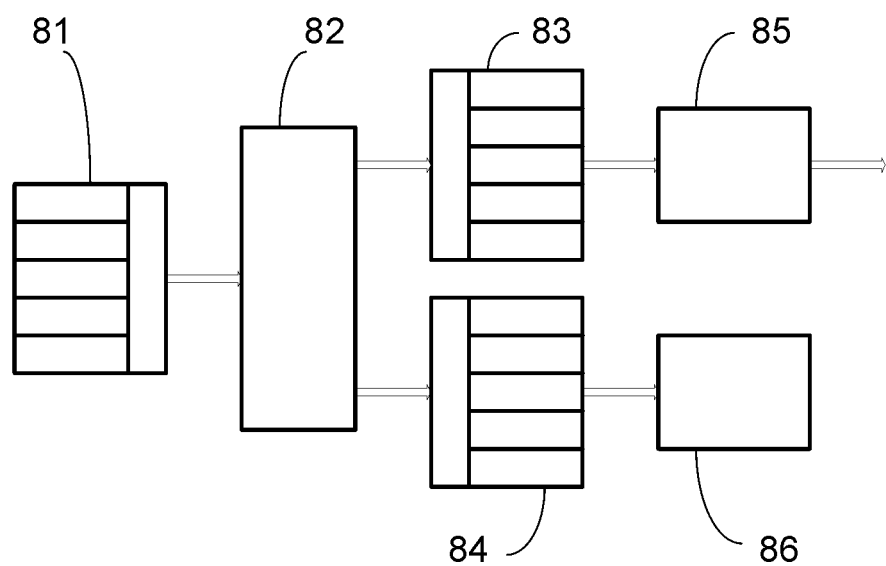

[Fig. 10]
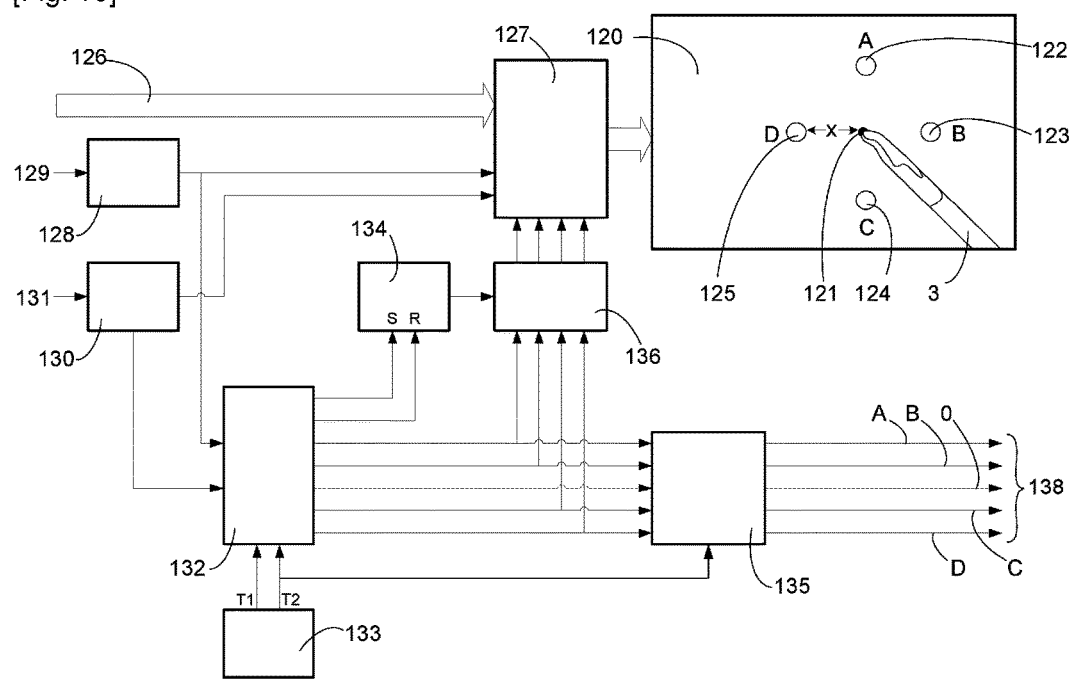

ENDOSCOPIC IMAGE PROCESSING SYSTEM HAVING MEANS WHICH GENERATE GEOMETRIC MEASUREMENT INFORMATION IN THE DETECTION RANGE OF AN OPTICAL DIGITAL CAMERA

BACKGROUND OF THE INVENTION (a) Field of the Invention

The invention relates to an image processing system of the kind specified in the pre-characterizing portion of claim 1, which is suitable in particular for medical purposes.

(b) Description of the Related Art

Such image processing systems are used today, for example, in the form of digital endoscope cameras both in general technology— for hard-to-reach repair sites— as well as in minimally invasive surgery. By the short focal length of used cameras, they have a relatively large depth of field, which is also necessary in order to provide a good overview of the working area to the operator and the considered objects not with every movement of the endoscope from the sharpening area appears. The corresponding cameras have a fixed distance setting that is adapted to the work area. The depth of field may include known systems, for example, a range of 1 mm to infinity. Because the objects to a workspace—despite sharp display— located at different distances from the camera lens, the represented size on a replay monitor can be not used as reference for other elements which the workspace or implants. The true size of objects and the distances between them can be very difficult estimate so on endoscopic examination.

During the endoscopic examination of inaccessible objects using digital cameras there is the need to obtain more precise geometric information about the object i.e. to measure individual elements of the object in terms of metric units.

Known is a multibeam laser projection procedure, where laser markings being projected on the object, which are recorded together with the image data and which are filtered from the image data in al later procedure to calculate optical geometric length data in a later procedure to gain geometric information due to their arrangement in the image. In this way, statements about the distance of the individual laser markings from the camera optics can be made by a subsequent by a subsequent computer processing by means of suitable software.

In http://www.karlstorz.de/cps/rde/xbcr/SID-0A010A01-E6111DF4/karlstorz/3628419295_156329_156329_1.pdf (see page 46, accessible) a laser reference measurement system is described, with the laser markings can be created on the object, by means of which a scale display in the image of an electronic measuring system may be calibrated. This system can be used similarly in the medical image reproduction, as it has been described in http://www.egms.de/de/meetings/hnod2009/09hnod324.shtml. From the distances of the laser markings on the object the volume is to be determined.

In U.S. Pat. No. 6,891,148 B1 a system is described for the generation of parallel laser beams for the scaling of photographic images. Measures to influence the scale of the figure are also not planned.

The evaluation is not in real time, so that the results are not immediately available. Although the scope must not be pulled out from the access opening for the evaluation, there is still a significant work stoppage, which cannot be accepted in the course of a minimally invasive surgery e.g. Also a special endoscope camera comprising means for the production of laser marking is necessary, which appear at fixed positions.

In the thesis "Augmented Reality in Laparoscopic Surgery" by Marco Feuerstein, 2007, (http://nbn-resolving.de/urn/resolver.pl?urn:nbn:de:bvb:91-diss-20070619-622737-1-8) several concepts to provide additional geometric information for the surgeon in endoscopic operations are described. This data are obtained by tracking the position of the instruments used during the operation. This done by mechanical markers fixed to the proximal ends of the instruments, which are monitored by additional cameras from the ceiling of the operating room. The movement of the markers is evaluated by means of an appropriate data processing with respect to the video information from the camera. A generation of additional geometrical information regarding objects in the working space thereby is not possible. Instead, additional information is required by CT or ultrasound measurement devices to obtain reliable geometric data relating to the operating room. Only this additional information on the basis of various geometric measurements allow to carry out a scaling of the image of the endoscope camera with the optical image of the ultrasonic head is used to calibrate the geometric values determined by the other geometric measurements on the camera image which are not in real time. The thesis summarizes the techniques thus, used in the known operation robots.

Elaborate additional imaging procedures need to be applied in the described procedures for obtaining additional information concerning the operative area, which sizes detectable on other than optical basis.

From U.S. Pat. No. 7,794,396 B2 it is also known to change the zoom factor of an endoscope camera automatically due to the position of a surgical instrument captured in the image. There is no additional geometrical information complementing the image content of the camera that can be evaluated. An automatic geometric distances for the measurement of the operative area with a subsequent automatic image adjustment is therefore not provided.

In http://www.duettrs.com/imageServeraspx?contentID=14325&contenttype=application/pdf is an Surgical instrument, that has a scale calibrated in a unit of length. However, this is provided for visual readout of the human Viewer. The necessary transfers and evaluations must be performed manually and are subject to the subjective assessment. An immediate automatic extraction of objective geometric measurements from the site is therefore not possible.

From U.S. Pat. No. 7,206,006 B2 also an image processing system is known, adjusted with the one obtained distance information of the scale of the image to be reproduced so due to a distance measurement between the camera and the size of an object in the screen of a monitor may be rendered to full scale. It is the difficult to meet the relevant parts of the object, whose representation is essential in full scale measurement. In addition, a rangefinder within endoscopic imaging system is not feasible.

In the non-published patent application PCT/DE2010/050058 of the applicant is an image processing system described, which laser markers used to the scale setting of the image to be reproduced.

SUMMARY OF THE INVENTION

It is an object of the invention, to design an image processing system of the above kind, by means of which an operator during a observation with any normal endoscope camera on a monitor of playback is possible to carry out assessments in the operation field with great accuracy and measurements and to implement immediately to editing without requiring manual measurements in the interior by means of mechanical or electronic scales or measuring devices. Also, the measurement should be possible immediately during the monitoring, so that no still image for subsequent calculations has to be selected and edited in a separate procedure. This is especially beneficial for minimally invasive operations performed under endoscopic observation, where the burden of the patient should be kept low through a short surgical time. The survey should take into account the local scale of image information captured by the camera at the measuring point readily, without requiring subsequent conversions.

This object has been met by the measures specified in the characterizing portion of claim 1.

The invention is based on the recognition that an instrument used in an endoscopic investigation, which is in the field of view of the endoscope camera, used to automatically perform geometric calculations using data processing can invention, if it automatically to capture the proportions of the instrument and to normalize so that the image scale of objects in the vicinity of the instrument is known and can be used to automatically perform geometric measurements and calculations.

Terms used are as follows: the term geometric distance information forms the basis for the scale information, which in turn serves as a local scale factor to convert the local length dimensions in the image to real dimensions as a size representative for a geometric distance.

The term comparison information consists of illustrations of the surface of the distal section of the auxiliary instrument from different directions and forms the reference basis for the size adjustment of auxiliary instruments to determine its scale and spatial orientation in the image.

The term geometric reference information is the relationship between a reference point and the picture and defines the position of a geometric reference site (optical identification of a geometric location) of the pictured instrument in relation to the image origin of the figure The term cursor is the optical identification of the associated geometric reference location of the instrument in the image, if the stored image of the instrument with the display was matched and the reference point associated with the figure is transferred to the screen.

The term surveying information defines the combination of the local scale and the reference position.

As will be shown below, such measurements can be used for the direct estimation of size dimensions on objects or in relation with movements, including those of the instrument itself.

Without expenditure of energy in the observed space, it is possible to measure the image scale and the distance from the camera using an auxiliary instrument as a reference in at least an image position. From the size of the image of the distal area of a common instruments or instrument part in the ongoing playback is a known distance information is determined from the image and on the local scale of the playback of environment—through implementation in a survey information—closed. Other endoscopic applications, a working instrument may often be inserted by an additionally available accessory channel in the field of image processing of the camera.

The mentioned survey information is the benchmark for the image scale in the distal area of the auxiliary instruments. Thus, the image scale of the adjacent area of the object can be determined so there distances directly out metrological point of view can be detected from the image. It also a virtual measuring rod can be with the image of the distal end of the instrument visually, so that it can be moved with the instrument to perform measurements on the object, if the instrument detection in the image with the appropriate evaluation is continuously updated in real time.

No special custom auxiliary instruments are required. This "Visual information", forming a common instrument employed already in operation by comparison with its stored image, whose sizes being known as reference base is used for the measurement, Thus the "distance information" according to the invention can be derived directly from the image, no special physical measuring rod needs to be used. The operation instrument brought into contact with the area to be measured can serve as a reference base for the measurement. The only requirement is that the instrument used is known with respect to its outer contour (and thus its geometric dimensions). The crafting of specially shaped and "survey-grade" instruments, can be additionally ensured by appropriate certification, a high quality standard is respected in this regard.

Thereby by means of a section of the auxiliary instruments in the area of detection of the optical digital camera within the observation area by the image a geometric distance information in the reception area of the camera is generated of to be, that scale-forming impact by comparison with the stored image of the section of the auxiliary instrument. It is not necessary that the geometric distance information is readable or be removed in any other way directly from the surface of the instrument. The distance information can implicitly be achieved by matching the camera image with the stored comparison image of the instrument. The scale factor in this case is not determined from a measurement taken from the image data, but directly from the factor, to be set in the size adjustment.

If the tip of the auxiliary instrument acts as a "Pointer", is a reference point for the calculation of the local scale is displayed in the image as cursor controlled with the end of the instrument.

Memory are particularly provided for a picture of the relevant section of the auxiliary instruments as comparison information for the purpose of matching with the current image of the camera views from different directions in coarse and fine presentation or means to the appropriate demand reduction of the stored illustration image information. This is any data representation which is able to find a reference to find the figure of auxiliary instruments and the relevant part in the recorded image of the camera. This may be particular to a complete representation of the surface of the end area or a corresponding three-dimensional representation, where this is preferably tailored to the comparison procedure used. So pixel or vector methods are suitable, as they can also be used for methods of content-based image search with the appropriate mathematical procedures.

Thus in the area of detection of the optical digital camera a geometric information produced, which is processed and then detected together with the image data and used to create additional geometric data concerning the image contents as survey information. The survey information is derived from a figure of the auxiliary instrument, which can be formed as normal surgical instrument, where the image of a part of the auxiliary instruments is extracted from the camera image and serves as a benchmark for a scale factor. On the basis of this scale factor an additional geometrical information inserted in fixed geometrical relation to picture of the auxiliary instrument in the current camera image as a virtual measuring or display element. Usually this will be a cursor, indicating that the auxiliary instrument was captured and used for the formation of scale. For example, this can be but also a measuring rod that appears attached to in the image with the help of instrument and may be handled like a virtual measuring rod.

The memory means also contain a geometric reference point in fixed relative geometric mapping to an image stored in first memory means. This virtual reference appears after the detection of the position of the auxiliary instrument and its scale in the picture displayed as a reference position and optical identification by type of a cursor in the current camera image, to obtain a defined reference point for the positioning of the instrument for measurement purposes.

This reference point defines the starting point for measurements and instrument movements to be tracked. It is preferably located at a protruding portion of the instrument, which may directly contact the body tissue during operation, so that this may be used as the reference for the calculation of the local image scale. Thereby the point of calculation for the local scale is closely linked to the section of the instrument adjacent object being the basis for the calculation of the local scale.

With the first detector means for the location of the general position of the relevant section image of the auxiliary instruments in the current camera picture for a coarse comparison with the image of the section of the auxiliary instruments memory the current position of the instrument in the camera image is roughly detected. If the general direction of the auxiliary instrument the running image and template coincides the location data is saved in the memory which initiates the fine detection of the second detector means.

With the second detector means for the fine adjustment to detect the size and orientation of the stored image of the part of the auxiliary instruments in relation to the corresponding figure of real auxiliary instrument section in the camera image. This is taking into account the exact position, the size the perspective distortion, and the direction of view. This is achieved a by means of an iterative selection of templates from different views from different directions and shifting the camera image in different coordinate directions while the size of the template is simultaneous changed. When the exact position of the auxiliary instrument and its orientation and size in the camera image is detected, the position of the interesting section of the instrument is accurately captured and the exact position and size data are stored into the memory and the distance from the camera and the scale factor of the section of the auxiliary instrument are set for further use.

Now a "virtual" graphic element to be inserted into the current image is to be generated. The, in size and orientation is adapted to the controlling auxiliary instrument and is—in the viewer's vision interacting with the other elements within the contents of the displayed image. That is, for example, suitable for measurements or more complex calculations that can be performed depending on the position of the virtual graphics. It is important that the graphics of the position and orientation of the relevant section of the auxiliary instrument is dependent on so that it fits true to scale in the image and the measurements can be performed also to scale. The virtual graphic element s— as previously mentioned— represents a measuring rod outgoing from the end of the instrument, which is parallel to the image plane (i.e. perpendicular to the optical axis). Is about the size of the adjacent section of the auxiliary instruments— taking into account of the its orientation in space— determines the local scale and a corresponding division of lengths units (in a unit of length to be selected freely) represented with the measuring rod, so that the user can use this measuring rod by a corresponding movement of the instrument such as a measuring rod.

The comparison of the section of the auxiliary instrument in the camera image with the respective image in memory, and to detect correspondence, appropriate detection criteria and standard mathematical techniques are to be used, as they are standard in the image processing technology.

Thereby a large number of additional information can be achieved through the optical analysis of the image of the auxiliary instrument inserted through an additional opening in the field of image of the endoscope camera and its subsequent processing of the captured image of distance, which would not be available by direct viewing. The online evaluation of the resulting data from the camera image into the displayed image in real time enables the operator to include the findings into his decisions immediately during the current operation.

It may also be particularly advantageous that a size assessment, adaptation and selection of implants can be made directly with the existing means of representation in the sterile area of the operating room. Also the information about the position of the instrument includes that these data can be the basis for a system to track steps (tracking, data logger).

By means of the use of two instruments represented in the image—a virtual connection in the form of a straight line connecting the ends of the ends of the tips of the displayed images of the relevant distal portions of the instrument may be displayed in the displayed image. In association to this line shown in the image, the length of the connection line may be calculated and digitally displayed in the image close to the local position of the distal ends of the two instruments determined on the basis local of the local scale factors. The local scale factors are different, at the positions of the two ends of the instruments the calculating must be based accounted by averaging the two scales factors. Also, the distal ends of the two jaws of pliers can be used instead of the two separate instruments.

If the object plane in the image is no orthogonal with respect to the optical axis of the camera the scale of three points in this plane have to be evaluated. The lines connecting the three points are defining a triangle. The scales at two of these points can be determined by evaluation of the tips of two auxiliary instruments as it has been described before. The scale at the third point may be determined by using an endoscope camera with an additional laser source, as it is the subject of an earlier patent application of the same applicant. The third scale value for the current image may be gained the image to convert the representation of the object plane into a displayed reproduction of equal scales by the application of an adequate trapezoidal (keystone) equalization twice.

A line produced by an adequate laser beam source having an adequate cross section, generated by a laser source fixed at the auxiliary instrument by an angular projection on to the object A contour line may be produce from camera's point of view, which allows an assessment of the topology of the object shown in the camera image. This is particularly useful in detecting columns or cracks in the object to achieve a scaled measurement for repair purposes.

The system according to the invention is suitable not only for endoscopic applications, but also for open repairs where the work area of the work piece for immediate adjustments is not accessible— unless he is too sensitive for repeated manipulations, or unless, that their surface properties become visible through an additional image processing to the human observer. Open operations in which want to customize implants without repeated fitting while avoiding direct contact with the patient's body would be in the medical field.

With the inventive image processing system not only measurements and scale adjustments can be achieve in the site, but the auxiliary instrument can be used as a pointer (cursor) or the function activation. Because also a location identifier of the geometric location of the distal reference location of the instrument in the image is displayed with the detection of the position of the instrument in the picture, the instrument as a "mouse replacement" could cause a feature selection and control via menu selection or through gestures with geometric auxiliary sizes for orientation in the image are displayed. It is important that the reference distances of this auxiliary variable to the orientation of the intimations in the image are adjusted current image scale so that movement strokes are constant run across the screen to be monitored, with the instrument. Ensures, that—according to the operation available standing space small and constant lasting movement strokes in the respective image scale in be detected and processed the image.

Doing adjuvants to change the image size that is rendered on the monitor or by comparing distances according to the local scale factor are provided depending on a digital zoom for the geometric distance value is an input value, for adjusting the image size on the screen according to a scale factor, the representative for a given geometric distance information as a multiplier is involved in the set so that an object that is contained in the image content, corresponds to the geometric dimensions of the given geometric distance, is rendered on the monitor with a corresponding dimension that is multiplied by the specified scale factor.

By comparison with the instrument in its current position in the image allows not only the measurement of the in the represented object in real time, but also allows more real or hidden in the image objects taken from the image or distances, a movement of real objects criterion form the local image scale to refer to, where the object is located, on this way objects or events, geometrically correct to process in the current image.

Besides the use of a virtual measuring rod with a customized lengths division, also the processing of distances of movements of the auxiliary instrument as a cursor or gesture element may be processed correctly by making use of the picture information in such a way, that matching distances are correctly evaluated by means of known scale factor of the image.

Also physical values as tension or pressure forces may be measured by observing and determining scaled distance on the instrument if this is as a measurement tool. This may be effected if the geometric surface of the instrument changes in physical size when responding to an outer physical effect i.e. a pressure or a tension analog to a spring action. A spring scale will serve as example, the excerpt length is proportional to the force acting on them. By means of the invention the elongation of the scale in the picture, can be taking into account and the respective record scale is to be captured image of the camera. Independent of the actual position in the image the physical value to be detected can be correctly measured and evaluated by using the correct scale factor determined according to the invention.

It is also beneficial, to use the arbitrary movements by detected instrument as a gesture function to the control functions within the system like a mouse in a PC-system. As such the opening or closing of the jaws of a surgical forceps may evaluated as the activation of a mouse button in a menu structure as a command when ends of the plier jaws each recognized as an instrument of part of, each assigned a reference point and the distance of the points of interest in the image plane each "measured" according to the determined local scale.

The benefits of the measures specified in the claims arise also on hand of the following examples.

Such advantageous embodiments of the invention are represented using the drawing closer and described in greater detail below. It show:

BRIEF DESCRIPTION OF THE DRAWINGS

FIG. 1 the principle of a first embodiment of the invention system with a surgical instrument and an endoscope camera.

FIG. 1A the visible in the screen representation of the configuration according to FIG. 1, FIG. 2 a block diagram as a working example of an evaluation circuit according to the invention.

FIG. 3 an extended block diagram as the embodiment of the invention with other ways of signal processing, FIGS. 4 and 4a the principle of an embodiment of the invention system with two surgical instruments and an endoscope camera in the block diagram, FIG. 5 a block diagram of the embodiment in accordance with FIG. 4, FIGS. 6, 6a and 6B three representations of embodiments of auxiliary instruments 10 in accordance with the invention, FIGS. 7 and 7a another variant of auxiliary instruments in accordance with the invention.

FIG. 8 further block diagram to the signal processing in accordance with a training of the invention, FIG. 9 working example of a surgical instrument in helping with means for detecting tensile or compressive forces, as well as FIG. 10 working example of an arrangement for controlling functions directly through the auxiliary instrument using gestures or choice of menu, where the movement distances in the image of the size of the representation of the auxiliary instruments are adapted.

DETAILED DESCRIPTION OF THE INVENTION

In the first embodiment of the invention shown in FIG. 1 an object 1 is in the recording pane of an endoscope camera 2, which is here represented in two droves of intersecting straight lines. The camera has an optical axis 21 and their shooting range is limited by a cone, which is represented by its boundary lines 22 in the picture. A mapped object with increasing distance from the camera is significantly decreasing its size with respect to the image of the endoscope camera because of its usually short focal length, which is associated with a significant change in scale, so that precise measurements using the recorded picture information are not readily available. An auxiliary instrument 3 forming a grasping forceps has a shaft 31, using 32 and 33 (distal) working end, which can make, for example, the legs of the surgical forceps.

In FIG. 1a is shown the corresponding image on the monitor, as seen by the surgeon. Accordingly in top view, the camera angle, an insert 32 as a carrier of the (distal) working end (jaws 33) section of the instrument 3, the shaft 31 and use a virtual reference point 101, which is located near the end of the instrument and is situated at the real point at which the instrument at normal attitude would affect the object 1 is electronically inserted into the rendered image on the object 1. In addition— virtual— an outgoing from the reference point of 101 beam 102 which 103 is equipped with scale markings is inserted in the image. This beam of 102 runs in the simplest case in the image plane in the direction of the plier jaws sequel, so that he can be controlled with the orientation of the real jaws in his direction.

Is shared by each two millimeters in length sections, for example the graduations on the beam and adjusts itself so that it is adapted in the image playback on the scale of the object in the reference point 101. This adjustment is— like its hand by FIG. 2 is described in more detail in the figure of the distal area (jaws 33) the auxiliary instrument 3 derived. Thus the surgeon can 11 the positioning of the auxiliary instruments in contact with the object— such as with a real gauge— length measurements make, which decreases the scale with the distance of the distal end of the auxiliary instruments from the camera lens. In this way can be obtained precise information about the size of operation objects, so that on the one hand, a precise logging is possible and also implants e.g. can be selected precisely. In the content of the image an additional ad is inserted so virtually, based on a distance information, which is derived from the figure of auxiliary instruments in the camera image. The appearance of the virtual display in the picture is also the confirmation that the electronic analysis— following to— was carried out properly. So that an immediate control of the correct functioning of the calculation is given. The surgeon can fiddle with the virtual scale so as with a real gauge is connected to his instrument. This would affect him but in his way of working. The virtual gauge he can demand and turn off. He is electronically controlled depending on the location and orientation of the instrument generated suitable and precisely indicates the length to be measured on the measuring object shown in the image in the selected unit of measure.

In FIG. 2 an embodiment of an evaluation circuit is shown as a block diagram, which is the means to process the geometric distance information in accordance with the invention. The visual image information in form of output signal of the endoscope camera 2 is continuously fed to the monitor 100, which receives the regular ongoing video information without interruption in real time. The signal is also fed to a single image storage unit 101, holding a single image from the current video signal for processing. This is used as the starting point for the following data operations to be described in detail. These operations are considerably accelerated when after recording a still image of a section of the auxiliary instruments as a reference, after its location has been detected for the first time and the image is held for recalculations only signal differences on the basis of current movements evaluated are calculated so that the movement of the instrument may can be easily traced.

The single image recorded in the single image storage unit 101 in a first comparison unit 102 (coarse) detector means is traced for the presence of a portion of the image, which is identical to the image stored in first memory unit 103 of the distal end of 32 of the auxiliary instruments. This comparison image is located in the memory segment 103a. Here, a search algorithm is used in the comparison unit 102, as used in content-based image search. The search criterion is coarse first, i.e. out of focus, and is preferred to an easily identifiable segment of the instrument 3, as, for example, the direction of the shaft. Is the information of the storage unit made 103 as depending on a "template" by continuous rows and column offset of the image contents in memory 101 and after subtraction of the respective memory contents to compare each won a kind of difference image, which passes to a subsequent evaluation unit 104 as detection means. Exceeds a predetermined threshold value currently a match criterion, which is determined by an inverse integration over the obtained difference image of the selected section of the instrument, a trigger signal with the reference point of the finding in the evaluated camera image is issued by a detection stage 105. While the match criterion is satisfied if the difference image is weakest. Adequate correlation techniques may be used.

In the memory 103 in association with the in the memory section 103a recorded "Search template" a reference point is detained, which communicated via the link 107 of the comparison unit 102, to determine the restricted search area. As explained, the reference point here outside of the comparison image held as a search template can be, like it is shown in FIG. 2A.

It has to be pointed out, that the comparison images held in the memory of 103 also may be the corresponding outline of the instrument, which, where appropriate, is sufficient to locate the desired item in the original image.

If the shaft 31 (FIG. 1) the instruments on the screen held in the storage unit 101 is determined, is due to the found location of reference operated a frame unit 106, which selects a smaller image area from the existing memory 101 image content, the found reference point surrounding, by reducing the amount of data to speed up the subsequent fine detection. If— as in the considered example— the distal portion of the auxiliary instrument, used for the fine detection, not with the area was used when the coarse detection is identical, so a geometric dislocation between the reference point (shaft 31) found first part's and to search for distal elements (jaws)— with the fine tuning— carried out in the selection of the image area is made, as it corresponds to the real situation. This would be a shift in the location of reference in a search scope at the end of the shaft, bearing the jaws, and nearby to the Center and in the example shown In the selected part of a fine tuning of the distal end of the instrument with another in the memory of 103 b down detailed images will then forward taken, which are presented here in detail. Here is a range of views from different directions and different size available. When the made is also a rotation in the axis of the direction (i.e. perpendicular to the viewing plane) and a shift in two coordinate directions, so compare the object to locate in all its possible forms. This is a correlation technology which emits a signal of the found similarity. This exceeds a predefined trigger value and represents the absolute maximum of the other match values resulting, so fired applied image size, the orientation of the coordinate and in addition the swivel angle around the axis of the direction here. The position and orientation of the concerned section of auxiliary instruments held camera pictured is clearly defined by a reference point of the comparison image chosen by the match criterion, and an associated direction vector, whose magnitude makes the scale information.

The direction vector is determined by the direction of the comparison image and its rotation in the image plane. Starting by the end of this vector a reference distance information, which is provided in the second storage media, sets the relative geometric mapping between the starting point of the vector that is characteristic of the found comparison image pictured held camera and the location that is inserted as a virtual reference point for the instrument part of the displayed image. For simplicity, this mapping of virtual datum in each of the images is fixed. According to each of the comparison images from the different directions is the focal length of the used endoscope camera pictured perspectival distorted, the reference to the virtual aperture in the camera image arises directly from the stored comparison image, if it was brought by finding the position with maximum compliance in a fine detection unit 108 through image selection, size variation and move correctly in accordance with the image captured by the camera. The point where the product touched a neighboring surface is so solid and can be displayed directly in the current image based on the information held in the memory of 103 *c*. Also a reference direction, which corresponds to the orientation of the auxiliary instrument is firmly connected with the found image. Normally, this is the orientation of the plier jaws.

Based on this data, a virtual information is read out from the second memory of 103*c*, adapted in size by the scale factor in the current video image is recorded directly or in conjunction with the pinned 14 still image as a picture-in-picture information on the mixing unit 109 in a corner of the current image in the monitor 100 is displayed.

Also an additional information, such as the pictured radial measuring rod from a corresponding memory 110 is inserted into the current image via a zoom stage 111 and an image synthesis stage and recorded in adequate scale.

It may be seen that in this way the surgeon during surgery without additional measures— alone through a specially crafted image processing— measurements can be made in the operation field.

In this first described example it is assumed that the measurement plane is extending in parallel to the image plane, because the reproduction of the measuring beam appears in true scale.

It is further comprehensible that the finding of the section of the auxiliary instrument will also, facilitated when its position in a preceding image is held and in the pictures following images only the area of the previous position in the camera image will be scanned.

The finding the of relevant section of the auxiliary instrument of may be still improved in so far as the comparison images held in the memory can be relocated or partially overwritten with these actual image of the relevant part of the current picture.

Instead of single still pictures from different space directions in the comparison memory also a coherent representation of a three-dimensional model cam be provided, which is adapted, enlarged, reduced according to a three dimensional CAD representation depending on the direction of viewing or movement.

Before starting the operation the image data of the instruments to be used will be transferred into memory or selected for use. Instead of an overall picture of the relevant section of the auxiliary instrument only contour images may be stored and compared.

It is apparent that if appropriate similarity criteria are used also stains on the instruments will not cause a failure of detection with a criterion of maximum similarity for comparison. This will especially be true if a self-learning technique and a trace of the instrument section is applied basing on the preferred consideration of the latest discovered position.

The system so far shown allows so, a common surgical auxiliary instrument without significant changes to control a virtual measuring rod use to which point of reference starting from one of the surgical instrument in helping virtually connected in the surgical field measurements in the image plane measurements perform, which adapted the measuring rod on the image scale 15, as it is found at a distance from the camera, where the virtual point of reference of the auxiliary instruments located. The direction of the measuring rod follows the alignment of the instrument, resulting in an ease of use.

Arrow 113 in FIG. 2 indicates that in the rough determination of the location of the instrument with the detector means 102 according to FIG. 2 not getting out of the entire camera image must be assumed. The requested section of the instrument is first found, it is sufficient to visit only the surroundings of the village motion of the same in the next search cycle, where the instrument section previously was. In this way, it is possible in the current image the measuring rod— or an appropriately dazzling others a graphic information, which, for example, a numeric value can be up to date with the position of the instrument to carry it.

In FIG. 3 is presented a more complex system, pointed out the ways in which should, as with the in FIG. 2 represented agents found information about another, expanding the information of the treating surgeon representations be complemented can. Here different graphics or measures derived from the current image to scale, can be inserted according to selection and recruitment through appropriate controls in the current image or an additional statue that representation is displayed depending on a PiP (Picture-in-Picture) representation.

That may be appropriate if within the image scale to perform computations, which go beyond the pure dimension supporting the current handling. To for example, area, and volume calculations performed or recorded measuring data in logs, go further than the pure real-time processing.

An operation of the photogrammetric or any other method which throws a graphical measurement or evaluation process, to start a trip unit 201 is provided, which can be initiated, for example, an external button that is attached to the camera unit along with other controls. With this trip is a still image storage unit 202 (comparable to the unit 101 in FIG. 2) of the current video signal of the camera 2 a single suitable image selected and recorded, that designed for further processing to actually. By means of an additional unit of input, that you want is selected by different graphic representations or procedures. This selection is supported by a cursor input unit 203, in which a local mapping can be made in addition. The output signals of the units 201 to 203 control a calculation unit 204, the 16 contains a graphics processor to implement the desired processing. Furthermore II is in block the processing part in FIG. 2 means are included. Hereby, so scale graphic information in mapping to the position of one (or more) instruments for auxiliary to further processing or presentation can be obtained.

The output signal of the calculation unit 204— depending on selected processing program—controls a graphics unit 205, are stored in the graphical representations, which complement the elements from the unit II (according to FIG. 2). These include evaluation window or menu selection fields for numeric data. The overlay in the image stored in the unit 202 is in the mixing unit 206, whereby an adaptation to the screen size to be emitted in a downstream zoom unit 207. The insertion as image of part of in the monitor playback is carried out in a PiP (picture in picture) mixing unit. Also the generated image on a separate tray Monitor 208 cannot be played, forming a separate playback device, which can be freely as a Wi-Fi-enabled Cordless screen in a desired display position. The control information for the special Tablet monitor 208 are mixed in a single unit 209, which mixed in another control unit 210 VII even the data from an Assembly, in FIG. 7 is closer. This is the log data, which derive from the movement of the auxiliary instruments for the purpose of logging and gestures data, also gained as the movement of auxiliary instrument— but serve the control of the system, as further described below in detail.

In FIG. 4 is shown in principle a survey by means of two instruments 3 and 4. With their end parts, 33 and 43 can be— such as on the basis of FIGS. 1 and 2 described— define reference points on the object 1 by appropriate positioning of the distal ends of 33 and 43 of their associated virtual tags (see the camera picture in accordance with FIG. 4a). The two instruments will identify through 32 and 42 labels attached in the form of circular rings of different number 34 and 44 in their operations. Other symbols on the instruments which identify themselves by means of other physical signal transmission can be can be attached instead these markings. These include, for example, RFID-tags.

The camera 2 is equipped with an additional source of laser, which emits a laser beam 48, which generates a laser marking 49 on the object 1. Whose distance from the intersection of the optical axis and the object of 50 defined a further benchmark for the determination of the local scale, as it is described in the earlier patent application of the applicant.

The object 1 should be in this example from a plane inclined in space which is not perpendicular to the optical axis 21 of the camera 2. A survey in the according to FIG. 1 displayed camera picture of the scale of the object that is rendered on the monitor is possible not readily, since depending on the distance from the camera lens— so is different in the different areas of the plane of the object 1. As on the basis of FIG. 2 shows also the valid points magnifications can be with the described measures calculated.

In FIG. 4A the corresponding monitor image is shown. Here the laser marking 49 is visible on the object, which is produced by a laser source that is attached to the shaft of the endoscope camera 2. Due to the known distance of laser marking 49 in the monitor FIG. 4a, which corresponds to the real distance of the laser source by the intersection of 50 with the optical axis of the camera, the magnification for this figure range can be calculated, as it is described in the earlier patent application of the applicant.

With the ends of 33 and 34 in FIG. 4A visible virtual reference points 51 and 52 are connected, which the end of a range to be measured 53 mark, which can be freely chosen by appropriate positioning of the ends of the tools 33 and 43 on the object 1. The distance 53 to measure appears in the current image as a connection of the associated with the instruments and associated with the virtual points 51 and 52, so that it appears as shown below— on the monitor. An additional digital display 54 is visible in the image, which currently digitally displays the length of the distance 53, calculated by the associated data system in a selected unit of measure. While other operations can be selected. Thus it is possible, for example, to evaluate also the area of the triangle is stretched by the points 49, 51 and 52 digital and displayed accordingly.

Because the object layer 1 to the optical axis of the camera 2 can slope any— unknown— that is so corrected screen that the plane of the object in skewed top view is represented, so would like located vertically in the camera. This is achieved here by a trapezoidal (keystone) distortion of the image in the way is made, that the environments of reference points 50 to 52 in the same scale are represented. This representation differs from that in FIG. 4A given again. The necessary calculation method will be described at hand of FIG. 5.

To be able to make a correct measurement level of the object— and thus on the screen, a trapezoidal (keystone) distortion correction is made in the arrangement in accordance with FIG. 5. Reference scale to the local scale at the laser marker 49 be. Now also environment of virtual points 51 and 52, which were determined in the same scale, appear to be about the geometry of the ends of 33 and 34 of the two instruments 3 and 4 according to above-mentioned principles is the picture this points in the direction of the opposite side of the dotted triangle with paragraphs 49, 51 and 52 in FIG. 4A correspondingly squashed or stretched. To a corresponding Keystone distortion is applied, optically mathematically but achieves a corresponding inclination of the to the opposite side of the triangle corresponds to the point in question, a distortion of the image, which to— in the direction of the Central vertical of each side of the triangle or decreases. In this way, the object 1 appears linearized such that length measurements can be carried out correctly on the screen. To make appropriate measurements and object comparisons in the original, the scale is set prefers a corresponding zoom operation on 1:1, so that in particular on the help screen in accordance with FIG. 208 3 immediate form adjustments can be made.

With respect to the embodiment represented in the FIGS. 4 and 4a must be auxiliary yet that the line between the virtual reference points 51 and 52 without trapezoidal (keystone) distortion correction and a third reference point 49 can be measured if it is not on the scale representation of the entire area, but only on the length of the straight line. In this case the length of the straight line with spatially awry reclining surface from the respective camera distances of the reference points 51 and 52 can be find, that after the rays rate calculated from the size of the figure can be.

In FIG. 5 is schematically shown a block representation of the data processing required (as part of the zoom unit 207 in FIG. 3). The local standards and image positions of the instruments or laser marking 50, 51 and 49 run to the blocks 301, 302 and 303 as input variables. This 304— is specified in the unit as above, calculated distortion on (double trapezoid) to be applied to the image. The current graphical representation is converted into 305 image memory and in the distortion unit 306, subjected to the distortion that is identified in the unit 304. The output is then about the other cache 307.

It may be comprehended that in the linearized on the scale object shown in top view 1 using suitable cursor means, which also— according to corresponding preset— by the auxiliary instrument or its associated data represented in the image can be made, in the plane of the object any points later tagged and measured are can, so that this evaluation it is bound, that an end of auxiliary instruments actually 19 will be performed on the object to the point to be measured. In the context of an operation, it may be sufficient for protocol purposes to touch the limits of a hernia or a tumor, gall stone, etc., to hold the data necessary for later measurement in continuing down to still images to the survey with the instruments.

Thus predefined movements of the instrument (in the air) can be interpreted as gestures by mapping pop-up menu (not shown here) on the monitor screen or by showing up an adequate text information— and also their combination as it will be is shown below on hand by FIG. 10.

In FIG. 6 is rendered a further embodiment of the distal end of an auxiliary instrument, whose distal end of 33 by the jaws of a surgical clamp made. These pliers' features that come with a surface in contact surface in the area of the bottom intervention means 60 laid down, allowing a holding action by a non-positive connection with a particular soft surface, so that the end of the instrument in the desired position is safe and secured against slipping. In this way, the instrument with slight pressure with an organic surface in secure contact can be kept, so that the measuring points with two instruments sure chosen can be fixed until the time at which the measurement is made. All those measures are suitable as intervention means, which prevent an unintentional dislocation on the surface to be treated, such as knobs, gears, profiles, scratches or roughened or knurled surface areas.

FIG. 6a shows a detail of the distal end of an embodiment of an auxiliary instrument for the application of the invention, which is particularly suitable as a reference and display instrument. The screen display is shown. The use of 32 is designed as bar-shaped area, carrying two scoops of 61 and 62 of varying diameters, arranged at a distance of 66 from each other. The remote outer ball 62 shows a smaller diameter 67 has the inside located ball (61) with a diameter of 68. The balls are extremely easy to identify because they have a same outline (with different diameters) from different directions in the image of the camera with digital evaluation means. So— connects with known dimensions and positioning of the figure of the balls in the camera image on their spatial positioning, the alignment of the instrument and the local scale. Virtual reference point is the end of 63 of the bar-shaped area of 32, which first comes into contact with a neighboring object surface, so that in this Fig. represented instrument particularly for exact positioned select measurement points, or for pointer applications is suitable.

The distance 69 are the internal reference information, which the removal of the external reference point of the instrument with an internal reference base (here the center of the lower sphere 67) in relationship. In the location of the outer reference position the cursor of 63 in the screen is generated that indicates that the instrument of 31 in his positioning was correctly recognized. The cursor position is relative to the external reference system of 64 of the screen on which the presentation is.

By matching the optical evaluation in accordance with FIG. 2 is especially easy because the balls 61 and 62 of all sides appear equal, so that no matter the axial alignment and therefore only a spatial direction must be taken into account. The execution can be used under difficult conditions or to the measurement of a system in accordance with the invention.

In FIG. 6b is shown, as not only the end of 33 of an instrument for determining a position and a local scale serve can, but with the instrument also a signaling is possible depending on a gesture if evaluates not only the position of the instrument in the camera image, but also its shape. This deformation is of the two jaws 64 in the example shown by the spread and causes 65, which can be triggered by end outside of the observation area of the instrument here. (The modified form is recognized in of the above detection and evaluation means instrument represented separately as an illustration.)

Where in FIG. 7 rendered embodiment of an instrument uses one on the usage of 32 in a the lower end of the shaft 31 adjacent end attached laser line source 71 by means of radiation 72, 73 different in his moderate-height extension in a field of 74 produces a linear laser marking 75. Where in FIG. 7 the camera image is recognizable, that through the figure of the laser line 75 because of it is oblique with respect to the optical axis of the camera meeting on the unevenness of 74 of the surface object 1 are considered recognizable.

If by the virtual data formed distance 78 laser line 75 is crossed by the, so can not only the straight 74 for measurement on the screen represented a second instrument 4 is kept, but also the laser line 75 due to the scale known dimension relationships to performing on-screen profile are converted, like it in FIG. 7A is shown. According to a perspective representation, as they can be in FIG. 7 is reproduced, with resulting measures.

Because the laser line at an angle on the (here represented in a stepwise inclination) object is projected, makes them from a camera perspective a contour line, which allows an assessment of the topology of the object captured by the camera. This is particularly in columns or cracks in the favorable object which should be measured accurately for repair purposes. A three-dimensional overview of the object can be obtained at a two-dimensional camera system in this way, without the need for lengthy subsequent evaluations. The topographic history of the surface is determined by the evaluation of the history of the laser line in the camera image on the basis of known mathematical relationships, and appears in the current image as a contour line. In this way, for example, the depth of cracks is there metrological exactly determine where they are hit by the laser line. This allows a precise assessment of the initiated measures the user defects.

In FIG. 8 based on the representation of a block is schematically shown, as log recording of instrument movements on the one hand a logging of operation history and on the other hand the evaluation of instrument movements can be used to control devices or other signal firings in the meaning of a gesture analysis. It is in both cases the consecutive storage instrument positions, and orientations and form conditions (see FIG. 6B) in temporal association. These states are logged with the associated timestamps in the memory of 81. Is it where appropriate in context and spatial mapping to an on-screen display— not shown here. According to the current system context is defined by previously made or more signal inputs or the currently displayed screen menu, the saved state data from the block reach 81 in an evaluation unit 82, where by comparison with prescribed time and location conditions the calculated result is evaluated by instrument locations and orientation either as a gesture to control predefined operations, which are addressable in a memory of 83 and passed for the purpose of execution of a control unit 85. The detected instrument locations and orientations but belong to a predefined scenario of an operational process, the label provided for this purpose in a memory for operation procedure is filed and the run on stored and passed to the output unit 86.

In FIG. 9 is shown in the sectional representation, how an auxiliary instrument 3 can be used to measure in such a way, that one on its surface visible change by changing the shape of the instrument about appropriate survey after may outside above will meet. The coverage 22 of camera 2 is positioned in the corresponding auxiliary instrument 3, the usage is tensioned according to a spring balance. A flexibly extendible area 91 is provided at the end with a hook 92, which engages in a flexible range of 93 of the object. To measure the tractive force transmitted to the object which is feather pull-out area about a manual tension of the instrument from the outer end pulled out until a necessary target load is reached. An optical evaluation of the instrument form, which is filed in the appropriate comparison memory different configuration is now via the camera image. In principle the detection of an "other" auxiliary instrument which is associated with the corresponding currently occurring load is for the different shape changes caused by the changing resilient excerpt respectively. Thus train measurements can be purely optical evaluation for endoscopic operations performed. A marking 94 enables assigning of used auxiliary instruments— accordingly, for example, the used characteristic of the provided tension spring for the evaluation. It is apparent that in a similar manner also measurements relating the submergence of an instrument can be made, if instead the 91 range a solid bar, where the length of the rest of is measured a deepening of outstanding— and visible to the camera part according to.

The evaluation may be performed as shown in FIG. 8, where different instrument types are evaluated instead of different instrument positions to be sought-after associated evaluation memory different readings in the, which can be transmitted in this way without auxiliary power or cable in the system, to which the camera is connected.

In the embodiment shown in FIG. 10 is an arrangement is displayed for the control of functions directly through the auxiliary instrument using gestures or menu selection. Functions of the system leaving itself immediately by corresponding movements of the distal end of the instrument trigger. It is not necessary to location the instrument to control the system. With the instrument tip only a space must be visited, which allows to run a relatively small movement in the image plane. This is required to trigger movement distances during image playback are adapted to scale of the size of the representation of the auxiliary instruments. In this way, it is ensured that the real run movements of the instruments is regardless of the size of the image on the screen, although the movement are evaluated on the basis of the digital data of image reproduction.

The user-visible scenery is shown in a snippet of 120 of the rendered image. The auxiliary instrument with its distal end is 3 away from the object, details of which are shown in the section 120 does not. The instrument is set with 3 in FIG. 2 represented arrangement with the given back camera 2 capture. The image data is processed accordingly so that the image scale in the range of the instrument 3 scale information as the position of the instrument tip as survey information in addition to the image data is available. In the picture of framing 120 a cursor 121 is reflected in the area of the distal end of the instrument 3, which moves synchronously with the tip of the instrument and measurement information displays the calculated position of the instrument tip in the image. The image of the cursor is created synthetically and forms a virtual marker on the distal end of the instrument. His appearance makes the visual feedback for the correct measurement and processing of the image of the instrument through the camera 2 in accordance with FIG. 2.

To be able to meet, to a feature selection from a menu selection fields 122 to 125 are labeled A through D in the image. Control functions of the system are associated with points (A) to (D) that now directly can be triggered by a movement of the instrument 3, in such a way, that the image of the instrument tip with the cursor reached 129 an of the selection fields 122 to 125 and superimposed on this at least in part. Through an evaluation logic further down to the associated function is triggered in this case. Examples of associated functions are: save a still image, start or stop a video recording or store a timestamp in the framework of a Protocol, or call of a submenu. The appearance of the selection fields is carried out at a distance x from the starting point, determined by the position of the cursor 129 in a short-time rest position of the instrument 3 is. Stops the instrument in a resting position, appears so set of tags 120 to 125 (distributed to the current position of the cursor 121) in the image, and indicates that a function selection can take location. Since the distance x depends on the marks from the starting position of the scale factor of the figure of the instrument 3 (x increases with increasing size of the representation of the instrument), ensures that the run to trigger a function means of the instrument in the image plane remain essentially the same regardless of the distance of the camera and the resulting image playback scale. An analysis of the movements of the instruments in the image plane would be possible without the presented marks that are used only for orientation, (pure gesture). In the sense of a complete menu can be displayed but also more detailed labels in the image or called submenus.

Now the function of the further block circuit 24 is described in more detail on the basis FIG. 10: the image information from the camera 127, reach a part of the image mixing via which the recorded image information overlay the synthetically generated overlays of virtual nature. From the block diagram in accordance with FIG. 2 derived data characteristic of the position of the instrument 128 for the cursor position entering a memory whose entrance of 129. In the memory of 130 for the scale (of the instrument display) the corresponding signal reaches from the block circuit according to FIG. 2 the entrance of 131. The reasons of simplification, be taken that the scale factor as the reciprocal value is transmitted, whose amount using the increasing size of the display also increases. By means of a detector and control circuit 132 you are raised necessary functions for image display for the menu— and gesture control. In the circuit of 132 signals to generate the display of tags are generated 122 to 125 in the image, the position at the distance x (controlled by the scale signal block 130) is moved to the position of the cursor (controlled by the position signal from block 128). A timer 133, which cyclically successively emits a clock signal to the times T1 and T2 is used for timing. Remains the instrument for a period of time that is greater than t1 (approx. 1 second), alone the output signal T1 to the setting input of flip flops 134, which switches the signals for the generation of tags 122 to 125 to the mixing part of the image via a switch 136, so that it is visible for the operator, that the menu or gesture control is unlocked. The display positions of markers of 122 to 125 for the period of t1 are now recorded in the control circuit of 132. A cursor movement, caused by a movement of the instrument in the image plane, which is not a the marks 122 to 125 achieved leads to time t1 by the corresponding signal to the control circuit of 132 and the reset input of the flip-flops of 134 to a reset of the two circuits in its initial state, so that no more function is triggered. So, small instrument movements remain without effect. The position of the cursor associated with the instrument tip reached the position of one of the marks of 122 to 125, those marks, whose position has been reached does not go out. Only the selected marker is displayed as a receipt for the successful selection. At the time T2 also the 135 will switch out, reducing the output including the display position for the selected marker to the logical switching levels, which raises the associated function with the pulse at the time T2 on one of the outputs of 138 in the system. This clears the display of the selected and activated display element on the screen.

If a measurement of the instrument is activated, as it is described above, it can be useful to record the measurement in a still photo. In this case, is the instrument to an active feature selection available. In this case, it is provided that this still photo is thrown if the cursor stays motionless easy to T2 in the center position and this position leads to a corresponding function activation via the "0" of the outputs line 138. The still photo can be prevented but if the cursor is over the instrument 3 only from the Centre moves away, without achieving one of the other mark.

It is perspicuous that also other functions this triggered, that which is turned the instrument axially and thus through the circuit according to FIG. 2 a different view to the alignment of the image of the instrument 3 is selected. The same applies to changes of the form of the instrument 3, such as one on expanding or closing the plier jaws.

The invention claimed is:

1. In an endoscopic image processing system comprising a digital optical endoscope camera with a large depth of field,
   means are provided for generating a geometric distance information in the form of an optical information, within the detection range of the endoscope camera this optical information being processed within at least one image (or partial image) of the current image information captured by the camera, being detected, separated from the image information and further processed, to obtain a measurement information from the image content derived from the digital camera,
   wherein
   the means being provided for producing the geometric distance information within the detection range of the camera, consist of
   the distal section of an auxiliary instrument being adapted to be held into the detection area of the camera and
   further means for the ongoing processing of the distance information are including
      memory means for at least one picture of the distal section of the auxiliary instruments as comparison information for the purpose of being compared with the actual current image information of the camera, and for a geometric reference information for the purpose of mapping a geometric reference location relatively to the stored image of the a distal section of an auxiliary instruments,
   first detection means
      to locate the approximate position of a picture of the section of the auxiliary instrument in the current camera image by its comparison with the image of the section of the auxiliary instrument recorded in the storage means and
   output means
      for the found position data, which are activated when a first match criterion is fulfilled,
   matching means
      for the size and orientation of the figure of the section of the auxiliary instruments stored in the storage means that includes views from different directions, with the image of the section of the auxiliary instrument within the camera image to achieve a possible reverse match through iterative selection of each one the different views from different directions and their relative dislocation with respect to the picture in the camera image in different coordinate directions under appropriate change in the relative scale of illustration by means of a corresponding mathematical modeling, basing on the position data found previously,
   second detection means
      to detect the coincident match of the spatially aligned through the adjusting means and size customized stored illustration of the part image of auxiliary instruments with the appropriate section of the camera image,
      to match the orientation of the found picture of the section of the auxiliary instrument in the camera image and its relative size compared to the stored image scale information when a second match criterion, and
      to output the survey information containing the geometric location information relating to the position insertion means
      to add an optical identification of the associated geometric location as a part of the survey information in the form of a cursor into the current camera picture at a position, which corresponds to the position in the camera image as a reference point resulting from the congruent overlay of the stored image to the current image of the section of the auxiliary instrument reproduced in a scale adapted due to the scale information being the read out reference information from the storage means.

2. The system according to claim 1, wherein the stored image of the section of the auxiliary instrument is a section of the surface of its shaft a level or a spatial marking affixed to it or its outer contour.

3. The system according to claim 1, wherein the stored image of the surface of the section of the auxiliary instruments in different views is a three-dimensional circular view or a number of side views from different directions.

4. The system according to claim 1, wherein the section of the auxiliary instrument includes at least a spherical area where in the case of two or more balls these are fixed in positions having a geometrical distance with respect to each other.

5. The system according to claim 1, wherein the fixed relative geometric correspondence among the picture stored in the storage media with a virtual optical identification a distal point as the reference point, which coincides with the tip of the auxiliary instruments, which first comes into contact when being approached to an external surface.

6. The system according to claim 1, wherein the auxiliary instrument is a surgical instrument in the form of a surgical forceps.

7. The system according to claim 1, wherein means are provided for adjusting the display size rendered on the monitor for an inserted image of a real or synthesized virtual zoomable object, a reference distance or the distance of the movement of an object in the vicinity of the reference point in being type a digital zoom are provided, for whom the scale factor from the geometric distance information is an input, for adjusting the image size on the monitor or calculating a distance according to the scale factor, to which a multiplier is included being representative for a given geometric distance information, so that an object contained in the image content, whose geometric measures corresponds to the given geometric distance, is rendered on the monitor with a corresponding dimension being multiplied by the factor shown with the predetermined distance or scale information.

8. The system according to claim 1, wherein that optical identification in the form of a cursor is a displayed element in an analog or digital representation in the form of a measuring rod or a distance measurement value respectively, with the representation in the form of a measuring rod displaying a scale in units of a length according to the detected scale factor.

9. The system according to claim 1, wherein means are provided, which are actuated by the detection of a given defined movement of the distal end of the auxiliary instrument and by evaluating the time changed position within the camera image to transfer a predefined value into the memory means.

10. The system according to claim 1, wherein means are provided to trigger the display of an analogue or linear distance value on a predefined movement of the distal end of the auxiliary instruments over a distance of a predefined distance through evaluation of their changes in position within in the camera image, where the displayed distance value is determined by the evaluated scale factor.

11. The system according to claim 10, wherein an optical marking is provided in the image, which indicates the end of the distance—basing on the reference position displayed by an optical mark at the distal end of the auxiliary instrument.

12. The system according to claim 10, wherein, when the surface of an observed object surface is not oriented in an orthogonal direction with respect to the optical axis of the camera the points of a triangle serve to as reference points, to equalize the image of the object surface on the monitor in such way, that the local scales of the areas of the object shown at the respective points of reference match.

13. The system according to claim 1, wherein, by the respective sections of two instruments two cursors are generated by means of which two points are to be marked on an object whose distance value is determined by geometrical calculation mines and is displayed on the monitor as a digital result.

14. The system according to claim 1, wherein the auxiliary instrument is a measuring instrument experiencing a change of outer form or contour depending on a physical effect in the, which allows for a reading and evaluation of reading of a the physical size of a determination of the length or shape comparison in the camera image.

15. The system according to claim 1, wherein, the auxiliary instrument is bearing a source for a laser being situated remote from its distal end, the beam having the cross section of a line, which is arranged in such a way that the line is directed orthogonally with respect the direction of the shaft of the instrument and direction of radiation is inclined with respect to the direction of the shaft of the instrument.

16. The system according to claim 1, wherein the monitor is a tray which is connected via a radio connection with an associated data processing device.

17. The system according to claim 1, wherein the representation is a picture in picture overlay with respect to the display of a monitor.

* * * * *